United States Patent [19]

Pálfi et al.

[11] Patent Number: 4,719,340
[45] Date of Patent: Jan. 12, 1988

[54] METHOD AND APPARATUS FOR THE OBSERVATION OF LUMINOUS PHENOMENA

[76] Inventors: Zoltán Pálfi, Keselyü u.l., H-1025 Budapest; István Fledrich, Munkácsy Mihály u. 3/A C/16, H-2100 Gödöllö; Sándor Krekács, Juhász Gy. u.2., H-1039 Budapest, all of Hungary; Sánder Bihary, 6690 Görding, Denmark

[21] Appl. No.: 9,618

[22] Filed: Jan. 22, 1987

[30] Foreign Application Priority Data

Aug. 25, 1982 [HU] Hungary .............. 2735/82

[51] Int. Cl.$^4$ .................................. G01J 1/20
[52] U.S. Cl. ............... 250/225 250/201; 250/225
[58] Field of Search ............ 250/201, 225; 350/330

[56] References Cited

U.S. PATENT DOCUMENTS 4,153,335 5/1979 Buchan ................ 250/225

*Primary Examiner*—Gene Wan
*Attorney, Agent, or Firm*—Handal & Morofsky

[57] ABSTRACT

Method and apparatus for the observation of luminous phenomena, especially for the observation of luminous effects excelling in the ambient luminous intensity by their high luminous intensity. By the present invention the above aim is fulfilled by a method and a an apparatus by which light transmission is varied depending on the intensity of the light effect futhermore, variation of light transmission is effectuated by a signal higher than the final control signal. The decrease of light transmission is fast and is in conformity with the intensity of the luminous effect, and lack or failure of external supply do not affect safety of observation.

5 Claims, 4 Drawing Figures

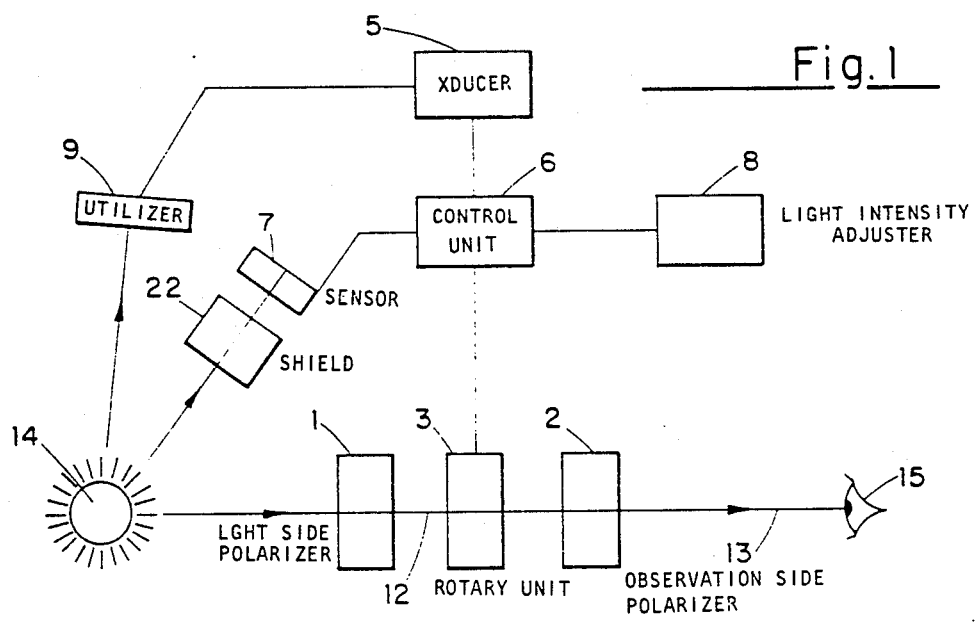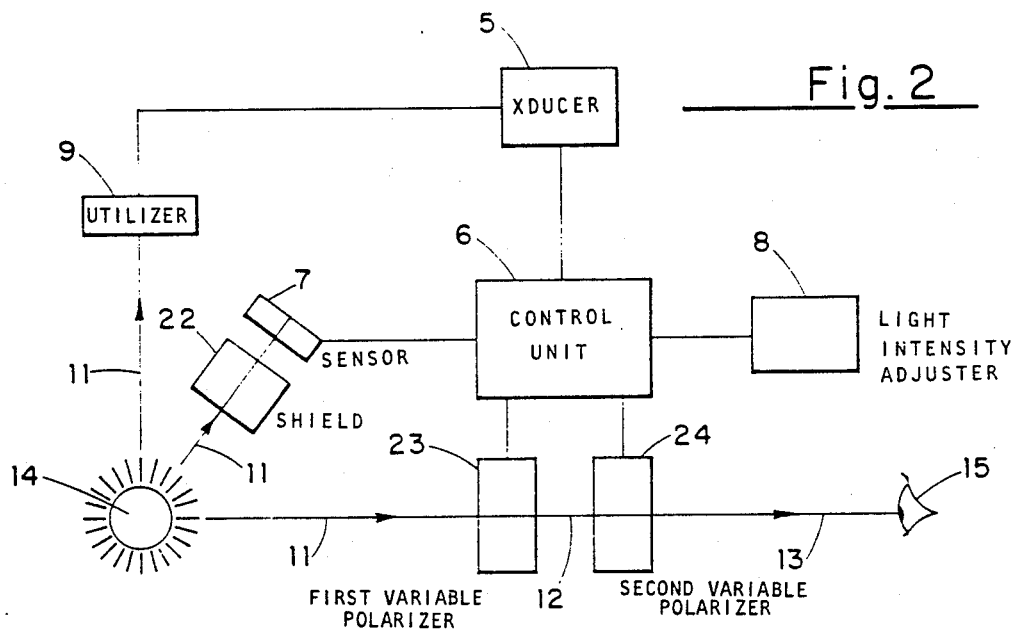

METHOD AND APPARATUS FOR THE OBSERVATION OF LUMINOUS PHENOMENA

This application is a continuation of application Ser. No. 608,863, filed Apr. 25, 1984 now abandoned.

TECHNICAL FIELD

The present invention relates to a method and apparatus for the observation of luminous effects excelling in the average ambient luminous intensity by their high luminous intensity.

BACKGROUND ART

During observation of such luminous effects, the sensitivity of most means of observation—e.g. the human eye—can be adjusted or it adjusts itself—within certain limits—to the intensity of the luminous effect to be observed. E.g. sensitivity of the human eye can automatically change or there is known such means of observation which can automatically change its sensitivity. This so called adaptation of the eye is physiologically limited and it often occurs such highly intensive luminous phenomena that cannot be observed without the serious damage of the means of observation, e.g. the human eye.

Such highly intensive luminous phenomena are especially frequent during heat power technological processes, i.e. welding or melting.

Naturally there are already several various means for the observation of luminous phenomena of especially high intensity compared to that of the ambient luminous effects.

Among such means with one or more light filters are in most common use at present, however, protecting means based on light polarization are ever more in general use. The unfavourable characteristics of simple masks and spectacles equipped with a light filter are well-known. Such an unfavourable characteristic is, e.g. that these equipment can usually be operated in two operational statuses, i.e. the protecting means is either inserted in or not. Consequently they are hardly suitable for the observation of luminous phenomena of variable intensity. There is another solution whereby reduction of light intensity to a certain degree can be achieved gradually, i.e. by inserting several light filters. The disadvantage of this means is that light intensity can only be regulated gradually, and it can be inserted by manual way or by a complicated mechanical solution.

Beyond these simple mechanical protecting means there are such ones whereas luminous intensity is reduced by optical grating or polarizers instead of light filters. The use of optical grating for such a purpose is not wide-spread due to its several unfavourable characteristics. The principle method of applying polarizers is that a liquid crystal is inserted between at least two polarizers angle of rotation of which depends on the applied voltage. Practical realization of this protecting means—e.g. in case of welding—is generally with two liquid crystal. Main characteristic of these well-known means is that the joint operation of liquid crystal is relatively slow, so a short overloading of the means of observation, e.g. of the human eye, is not excluded. Furthermore for the operation of most well-known means special voltage supply is required which harmfully effects operational safety, or the required operational safety can be granted only by special, expensive construction.

Furthermore, these well-known means can generally be operated in a binary way, meaning, that a luminous phenomenon of higher intensity than a preset value induces the means to reduce its light transmission to a certain value independently of the intensity of the luminous phenomenon inducing the reduction. In such a way the intensity of transmitted light is substantially changed.

SUMMARY OF THE INVENTION

Aim of the present invention is to avoid the above unfavourable characteristics by finding a solution by which light transmission of the means can automatically be reduced just upon occurrance of the intensive luminous effect to be observed and preferably with the possibility of operating the means without external voltage supply.

After attainment of the above, intensive luminous phenomena can be observed much favourably and with higher safety from the point of view of labour safety than before. Intensity of transmitted light is nearly constant depending on the present value independent of the intensity of the luminous phanomenon.

Task of the present invention is to find such a method and apparatus by which luminous phenomena of higher intensity than the ambient light effects can much favourably be observed as reduction of transmission is fast and corresponds to the intensity of the light effect, and lack or failure of the external supply does not effect the reliability of observation.

By the present invention the above task is solved by a method whereas light transmission is variable depending on the intensity of light effect, furthermore the initial variation of light transmission is effectuated by a signal higher than the final control signal.

Furthermore, by the present invention the above task is solved by an apparatus which is having a light transmission varying element and this element is inserted in a control circuit.

Furthermore, in a preferred embodiment of the present invention the light transmission varying element is a rotary unit, e.g. at least one liquid crystal inserted between at least two polarizers.

Furthermore, in a preferred embodiment of the present invention the light transmission varying element is at least one polarizer with variable position and/or variable polarizing characteristics.

Furthermore, in a preferred embodiment there is at least one sensor inserted in the control loop, whereas, e.g. the sensor is in connection with the rotary unit resp. with at least one variable polarizer in a direct way and/or through an RC network.

Furthermore, the above task is solved by an apparatus in which an impulse generator is inserted in producing a higher signal than the prevailing control signal.

Furthermore, the above task is solved by an apparatus in which, in order to ensure voltage supply, a solar electric cell or a photoelectric cell is inserted.

BRIEF DESCRIPTION OF DRAWINGS

The invention will now be described by way of example with reference to the accompanying drawings in which:

FIG. 1 is the outline drawing of the apparatus of the invention specifying an embodiment whereas the light transmission varying element is a liquid crystal inserted between the polarizers.

FIG. 2 is the outline drawing of the apparatus of the present invention specifying an embodiment whereas the light transmission varying element is composed by two variable polarizers.

DESCRIPTION OF THE PREFERRED EMBODIMENTS

Figure 3:
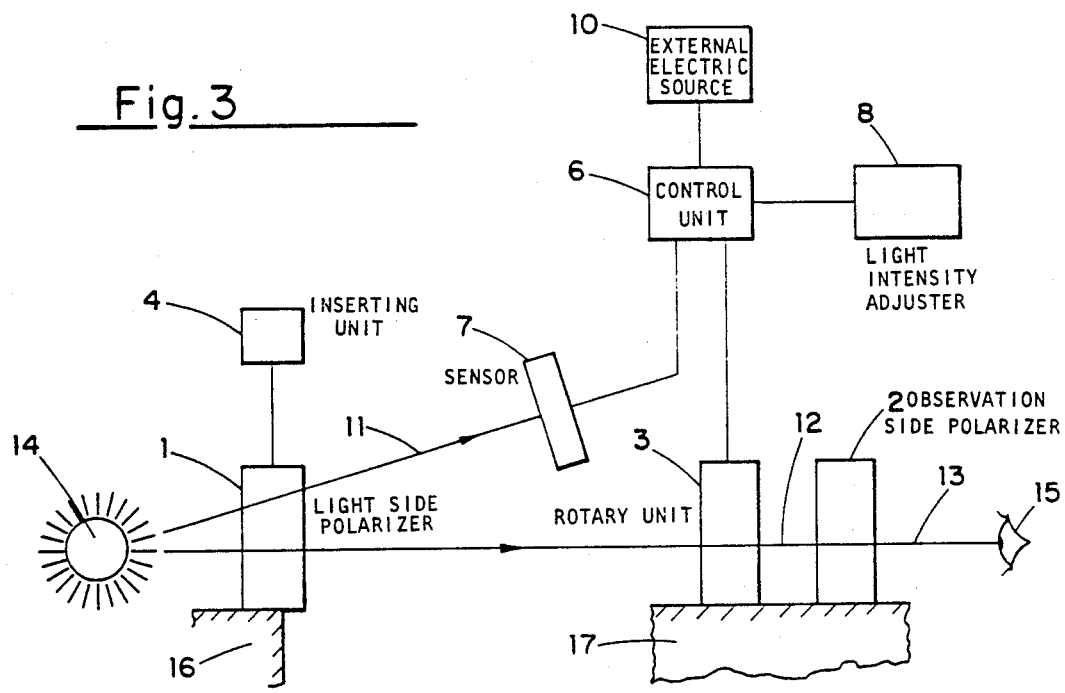
FIG. 3 is the outline drawing of the apparatus of the present invention specifying a design whereas at least one of the polarizers is mechanically independent of the liquid crystal.

The means of FIG. 1 involves a light-side polarizer 1, an observation-side polarizer 2, a rotary unit 3, a transducer 5, a control unit 6, a sensor 7, a light intensity adjuster 8, a heat or light energy utilizer 9 and a light source 14. The light source 14 emits a diffused light beam 11 which, passing through the light-side polarizer 1 is transformed into a polarized light beam 12, then, passing through the observation-side polarizer 2 and the rotary unit 3, it is transformed into a light beam 13 suitable for inspection, while in the heat or light energy utilizer 9 and in the sensor 7 they are producing electric signal or change electrical characteristics. In the surroundings of the sensor 7 there are shield 22 inserted in.

Principal operation of the above lay-out is as follows:

The diffused light beam 11 of the light source 14 is producing electric energy in the heat or light energy utilizer 9. Preferably they are thermoelectric or photoelectric cells. The energy produced in this way is transduced by the transducer 5 accordingly.

Sensing intensity of the light source 14, the sensor 7 shielded by the shield 22 gives a signal to the control unit 6 which, comparing it with the signal of the light intensity adjuster 8, forms a control signal which varies the degree of rotation of the rotary unit 3. The shield 22 grants that variation of light transmission is indicated only by the light source 14 while excluding ambient light effects. Depending on the position of the light intensity adjuster 8, the rotary unit 3, inserted between the observation-side polarizer 2 and the light, side polarizer 1 modifies, in reply to the signal of the control unit 6 the direction of polarization of light passing therethrough to such a degree that light intensity felt by the observer 15 remains at a prset, nearly constant level.

The control unit 6 as per FIG. 2 is connected to the first variable polarizer 23 and to the second variable polarizer 24. Characteristic feature of these first and second variable polarizers 23 and 24 that they can vary the degree of polarization and/or the degree of rotation of the axis of light or the degree of rotation of the polarizers according to the applied voltage. Operation of this layout is similar to that of FIG. 1 with the exception that light transmission is varied by the variation of the input voltage of the first and the second variable polarizers 23 and 24. It should be noted that it is not absolutely necessary—e.g. in a given case—to apply variable polarizers for both the first and the second polarizers, as a similar arrangement can be achieved by a permanent and a variable polarizer, as well.

FIG. 3 shows that in this embodiment the light-side polarizer 1 is in connection with the inserting unit 4 while this light-side polarizer 1 is arranged on the first supporting element 16. The rotary unit 3 and the observation-side polarizer 2 are mounted on the second supporting element 17 while the second supporting element 17 and the first supporting element 16 can separately be moved. In case of this arrangement the control unit 6 is in connection with an external electrical source 16.

Figure 4:
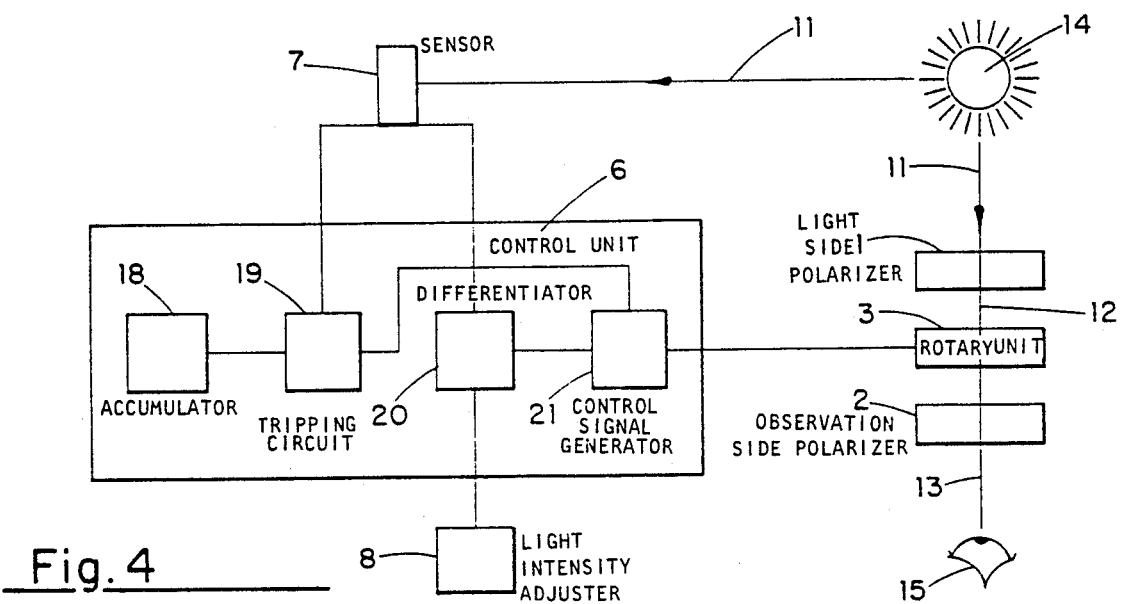
FIG. 4 is a principal block diagram of a light transmission control unit suitable for this purpose.

FIG. 4 shows the block diagram of a preferred embodiment of the control unit 6. The control unit 6 involves an accumulator 18, a tripping circuit 19, a differentiator 20 and a control signal generator 21 where the accumulator 18 is in connection with the tripping circuit 19, and the latter is in connection with the central signal generator 21, furthermore the differentiator 20 is also connected to the control signal generator 21.

Principle of the operation of the apparatus of FIG. 4 block diagram is that the high intensity light effect sensed by the sensor 7 controls the tripping circuit 19 which connects the energy stored in the accumulator 18 to the control signal generator 21 which produces a considerably steep control signal value of which exceeds that of the control signal corresponding to the signal produces in the differentiator 20 in reply to the light effect sensed by the sensor 7. In this way the rotary unit 3 resp. the variable polarizer is practically overdriven, so the required decrease of light transmission is reached in an extremely short time.

In case of some effective embodiments of the present invention there are several sensors 7 arranged, furthermore, the sensor is—e.g. in a given case—in direct connection with the rotary unit 3 resp. with at least one variable polarizer.

Advantages of the means of the present invention are the relative simplicity and the safe and fast operation.

We claim:

1. Method for controlling the light intensity transmitted through a light tranmsitting equipment (3,23,24) from a light source (14), comprising the sets of sensing the light intensity of the light source (14), controlling the light transmitting power of the light transmitting equipment in dependency of the sensing signal, said sensing of the light source (14) is is performed operatively before the light transmitting equipment (3,23,24) and said controlling of the light transmitting power of the light transmitting equipment is performed in comparison to a present value and said controlling of the light transmitting equipment (3,23,24) is effected at the beginning of a high intensity light effect by a start signal,which is different from and higher than the normal control signal,whereby an instantaneous decrease of light intensity transmission is effected.

2. Device for controlling the light intensity transmitted through a light transmitting equipment (3,23,24) from a light source (14), comprising a sensing element (7) placed behind a shield for sensing the light intensity of the light source (14), a power source and a control unit (6) connected to the sensing element (7) and comprising a control signal generator (21) connected to the light transmitting equipment (3, 23, 24), said sensing element (7) being located operatively before the light transmitting equipment (3,23,24), and wherein said control unit (6) comprises an adjustable setting means (8) for setting the light intensity passing through the transmitting equipment (3,23,24) and a start signal generator (18) comprising a tripping circuit (19) connected to the sensing element (7), the control signal generator (21) supplying thereto a start signal higher than the normal control signal at the beginning of a high intensity light effect sensed by the sensing element (7), whereby an instantaneous decrease of light intensity transmission is effected.

3. Device according to claim 2, characterized in that the start signal generator comprises an accumulator (18).

4. Device according to claim 2, characterized in that the power source is a heat or light energy utilizer (9) driven by the heat or light energy of the light source (14).

5. Device according to one of claims 2 to 4, characterized in that the sensing element (7) is connected through a RC-network.

* * * * *